United States Patent [19] [11] 3,966,765
Sircar et al. [45] *June 29, 1976

[54] PROCESS FOR PRODUCING BENZOTHIOPYRANS

[75] Inventors: Jagadish C. Sircar, Dover; Harold Zinnes, Rockaway; John Shavel, Jr., Mendham, all of N.J.

[73] Assignee: Warner-Lambert Company, Morris Plains, N.J.

[ * ] Notice: The portion of the term of this patent subsequent to Apr. 30, 1991, has been disclaimed.

[22] Filed: Oct. 11, 1974

[21] Appl. No.: 513,986

Related U.S. Application Data

[62] Division of Ser. No. 464,707, April 26, 1975, Pat. No. 3,878,198.

[52] U.S. Cl............................................ 260/327 TH
[51] Int. Cl.².................................... C07D 335/06
[58] Field of Search............................. 260/327 TH

[56] References Cited
UNITED STATES PATENTS 3,769,292 10/1973 Zinnes et al................. 260/327 TH
3,808,205 4/1974 Sircar et al...................... 260/243 R Primary Examiner—Sherman D. Winters
Attorney, Agent, or Firm—Albert H. Graddis; Frank S. Chow; George M. Yahwak

[57] ABSTRACT

β-Ketoacyl derivatives of 6-aminopenicillanic acid of the formula:

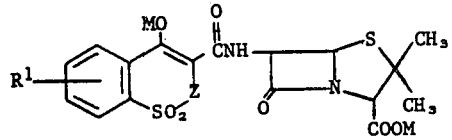

are disclosed. In the above structure $R^1$ is hydrogen, alkyl, halogen, alkoxy, cyano, trifluoromethyl and the like; Z is $CHR^2$ or $NR^2$; $R^2$ is hydrogen, alkyl, aralkyl; M is an alkali or alkaline earth metal such as sodium, potassium, or calcium. These compounds are useful as anti-bacterials.

1 Claim, No Drawings

PROCESS FOR PRODUCING BENZOTHIOPYRANS

This is a division of application Ser. No. 464,707 filed Apr. 26, 1974, now U.S. Pat. No. 3,878,198.

The present invention relates to semisynthetic penicillins, and more particularly it relates to β-ketoacyl derivative of 6-amino-penicillanic acid of the formula:

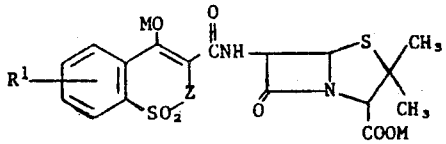

wherein $R^1$ is hydrogen, alkyl, halogen, alkoxy, cyano, trifluoromethyl and the like; Z is $CHR^2$ or $NR^2$; $R^2$ is hydrogen, alkyl, aralkyl; M is an alkali or alkaline earth metal such as sodium, potassium, or calcium.

"Alkyl" and "alkoxy" as used in the specification and in the claims are meant to have 1 to 7 carbon. These include, for example, methyl, ethyl, propyl, isopropyl, butyl, isobutyl and so on. "Aralkyl" encompasses alkyl as defined in which an aryl group of 6 to 10 carbon atoms is substituted for a hydrogen atom such as, for example, benzyl, phenethyl and the like.

The compounds I are useful as antibacterial agents. At concentrations of 31 to 500 mcg/ml they inhibit *S. aureus* and at concentrations of 67–500 mcg/ml they inhibit *N. gonorrhoeae*.

These compounds are accordingly indicated in the treatment of infections caused by these susceptible organisms. Generally speaking the dose for treating such infections in an adult is about 500 mg to 1000 mg orally or topically.

Compound I is formulated with dosage forms for oral or topical administration utilizing known pharmaceutical technology for preparing penicillin derivatives.

According to the process of this invention, 6-aminopenicillanic acid II is reacted with an activated ester of structure III, where $R^4$ is hydrogen or $NO_2$, in the presence of a base such as triethylamine. The initially formed triethylammonium salt is converted to the dimetal salt by treatment with a metal salt of an organic acid such as 2-ethylhexanoic acid.

The starting compound II is commercially available. The starting compounds III are prepared by the following scheme:

An enamine of structure IV is reacted with phosgene to give the acid chloride V. This is not isolated as such but is reacted with a phenol of structure VI to form an enamine ester of structure VII. Acid hydrolysis of VII gives the required activated ester III.

The preparation of the starting enamine IV is described by Zinnes, et al., J. Org. Chem. 31, 162 (1966) and in our patent application Ser. No. 251, 163 filed May 8, 1972 now U.S. Pat. No. 3,808,205. The compound III wherein $R^1$ and $R^4$ are hydrogen and Z is $NCH_3$ is also described in the latter application.

In order to illustrate further the practice of this invention, the following examples are included. Temperature is given in degrees centigrade.

EXAMPLE 1

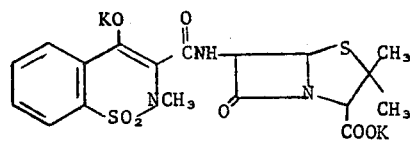

Dipotassium 6-[(4-Hydroxy-2-methyl-2H-1,2-benzothiazin-3-yl)formamido] penicillanate S,S-Dioxide A solution of 3.2 g (0.015 mol) of 6-aminopenicillanic acid and 6.0 ml of triethylamine in 25 ml of dichloromethane was cooled to 0° and 5.6 g (0.015 mol) of p-nitrophenyl 4-hydroxy-2-methyl-2H-1,2-benzothiazine-3-carboxylate 1,1-dioxide was added (as the solid powder) followed by 3.0 ml of additional triethylamine and 7.5 ml more dichloromethane. The reaction mixture was stirred at room temperature for 90 hr after which time the infrared spectrum of a small sample indicated that there was no further decrease in the intensity of the ester carbonyl band at 1690 cm$^{-1}$. Dilution of the reaction mixture with 100 ml of ether resulted in separation of an oil. The solvent was removed by decantation, the oil was dissolved in 25 ml of dichloromethane, and reprecipitated by the addition of 100 ml of ether. This procedure was repeated twice more and the resulting oil was triturated with dry ether to give a brown solid (the triethylammonium salt) whose infrared spectrum showed bands at 1760, 1600, and 1172 cm$^{-1}$, representing th β-lactam, amide and $SO_2$ groups, respectively. This crude salt was dissolved in 30

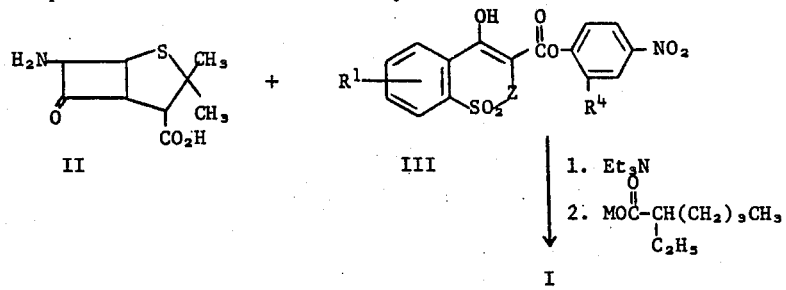

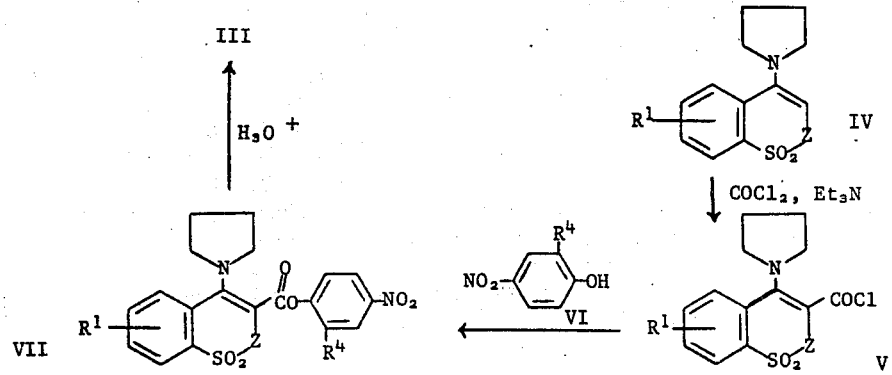

ml of methanol and 15 ml of a 2.4 molar solution of potassium 2-ethylhexanoate in n-butanol was added. Dilution with 100 ml of ether resulted in precipitation of the desired potassium salt. This was redissolved in 30 ml of methanol, the solution was filtered, and 100 ml of dry ether was added. The resulting precipitate was redissolved in 20 ml of methanol and reprecipitated by the addition of 50 ml of dry ether. The resulting precipitate was collected and dried in vacuo over phosphorus pentoxide at room temperature for 48 hr to give 1.6 g of product which did not melt but started to decompose at 230°.

$\nu^{Nujol}$ 3400, 1760, 1600, 1172 cm$^{-1}$. $\lambda_{max}^{EtOH}$ 234 ($\epsilon$6,400), 322 (5,600) m$\mu$.

EXAMPLE 2

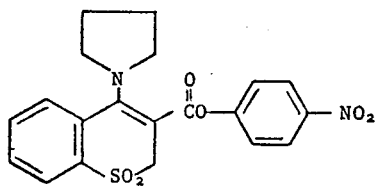

p-Nitrophenyl 4-(1-pyrrolidinyl)-2H-1-benzothiopyran-3-carboxylate 1,1-Dioxide

A solution of 6.0 g (0.06 mol) of phosgene in 55 ml of benzene was diluted with 30 ml of tetrahydrofuran and cooled to −10°. To this was added over a period of 30 min, a solution of 12.6 g (0.05 mol) of 4-(1-pyrrolidinyl)-2H-1-benzothiopyran 1,1-dioxide and 10 ml of triethylamine in 400 ml of tetrahydrofuran and the reaction mixture was stirred at room temperature for 3 hr. It was cooled to −40° and a solution of 7.7 g (0.055 mol) of p-nitrophenol and 12 ml of triethylamine in 50 ml of tetrahydrofuran was added. The mixture was stirred at room temperature for 16 hr, refluxed for 3 hr, and most of the solvent was evaporated. It was treated with ice-water and extracted ith dichloromethane. The dried dichloromethane phase was evaporated to an oily residue which became a gummy semisolid on trituration with several portions of ether. This gum was dissolved in dichloromethane. Slow distillation resulted in the crystallization of 13.0 g of product, mp 171°–174° dec. Recrystallization from a mixture of 250 ml of tetrahydrofuran and 250 ml of isopropyl ether gave 10.7 g of material, mp 175°–178° dec.

Anal. Calcd for $C_{20}H_{18}N_2O_6S$: C, 57.96; H, 4.38; N, 6.76; S, 7.74. Found: C, 57.90; H, 4.64; N, 6.83; S, 7.98.

EXAMPLE 3

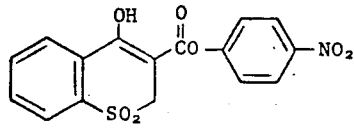

p-Nitrophenyl 4-Hydroxy-2H-1-benzothiopyran-3-carboxylate 1,1-Dioxide

A mixture of 7.0 g of p-nitrophenyl 4-(1-pyrrolidinyl)-2H-1-benzothiopyran-3-carboxylate 1,1-dioxide, 50 ml of glacial acetic acid, and 100 ml of 1N hydrochloric acid was heated on a steam bath for 20 min and diluted with ice-water. The resulting precipitate was collected and recrystallized from tetrahydrofuran-isopropyl ether to give 5.5 g of product, mp 206°–209° dec.

Anal. Calcd for $C_{16}H_{11}NO_7S$: C, 53.19; H, 3.07; N, 3.88; S, 8.87. Found: C, 53.19; H, 3.15; H, 3.64; S, 9.11.

EXAMPLE 4

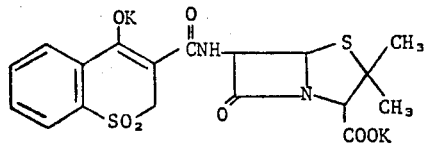

Dipotassium 6[(4-Hydroxy-2H-1-benzothiopyran-3-yl)formamido]penicillinate S,S-Dioxide A solution of 2.16 g (0.01 mol) of 6-amino penicillanic acid and 4 ml of triethylamine in 18 ml of dichloromethane was cooled to 0° and a solution of 3.8 g (0.0105 mol) of p-nitrophenyl 4-hydroxy-2H-1-benzothiopyran-3-carboxylate 1,1-dioxide and 2 ml of triethylamine in 10 ml of dichloromethane was added. The reaction mixture was stirred at 0° for one hour and then at room temperature for 20 hr after which time the infrared spectrum of a small sample indicated that the ester band at 1690 cm$^{-1}$ had nearly disappeared. Dilution with 75 ml of ether resulted in separation of an oil. The solvent was removed by decantation, the oil was dissolved in 20 ml of dichloromethane and rec-precipitated by the addition of 50 ml of ether. This procedure was repeated twice more and the resulting oil was triturated with 50 ml of dry ether to give a yellow solid (the triethylammonium salt) whose infrared spectrum showed bands at 1760, 1605, and 1160 cm$^{-1}$, representing the $\beta$-lactam, amide, and SO$_2$ groups, respectively. This crude salt was dissolved in 30 ml of methanol, 10 ml of a 2.4 molar solution of potassium 2-ethylhexanoate in n-butanol was added, and the solution was allowed to stand for 15 minutes. Dilution with 80 ml of anhydrous ether resulted in precipitation of the desired potassium salt. This was redissolved in 20 ml of methanol and reprecipitated by the addition of 60 ml of ether. This dissolving are reprecipitation process was repeated, the crystalline precipitate was collected, triturated with ether, and dried in vacuo over phosphorus pentoxide at room temperature for 20 hr to give 3.0 g of product, mp 235°–240°dec.

$\nu^{Nujol}$ 3400, 1760, 1600, 1158 cm$^{-1}$. $\lambda_{max}^{EtOH}$ 236 ($\epsilon$7,700), 338 (5,000) m$\mu$.

We claim:
1. A process for the production of a compound of the formula:

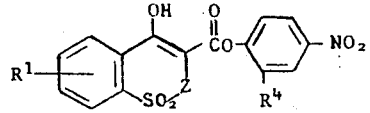

III wherein Z is CHR$^2$; R$^1$ is hydrogen, a lower alkyl of 1 to 7 carbon atoms, a lower alkoxy of 1 to 7 carbon atoms, halogen, cyano, or trifluoromethyl; R$^2$ is hydrogen, lower alkyl of 1 to 7 carbons, or aralkyl wherein the alkyl moiety contains from 1 to 7 carbons and the aryl is a monocyclic aromatic radical of 6 to 10 carbon atoms; and R$^4$ is hydrogen or a nitro radical which comprises:

A. treating a compound of the formula:

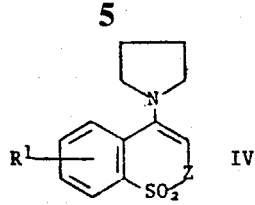
with phosgene to give a compound of the formula
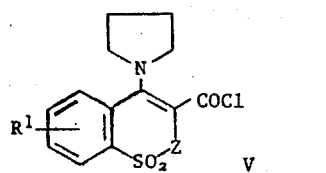
B. reacting compound V with a compound of the formula:
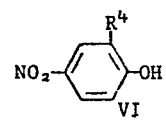
to obtain a compound of the formula:
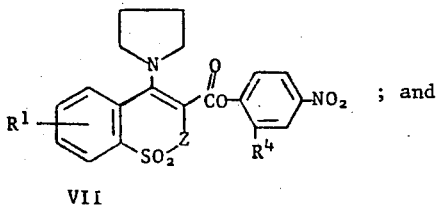
; and
C. hydrolyzing Compound VII under acidic conditions.
* * * * *